US008821509B2

(12) United States Patent
Piasecki

(10) Patent No.: US 8,821,509 B2
(45) Date of Patent: Sep. 2, 2014

(54) SURGICAL INSTRUMENT AND METHOD OF USING SAME

(71) Applicant: Dana P. Piasecki, Charlotte, NC (US)

(72) Inventor: Dana P. Piasecki, Charlotte, NC (US)

(73) Assignee: Danamed, Inc., Charlotte, NC (US)

( * ) Notice: Subject to any disclaimer, the term of this patent is extended or adjusted under 35 U.S.C. 154(b) by 31 days.

(21) Appl. No.: 13/662,475

(22) Filed: Oct. 27, 2012

(65) Prior Publication Data
US 2014/0121668 A1 May 1, 2014

(51) Int. Cl.
A61B 17/90 (2006.01)

(52) U.S. Cl.
USPC ........................................................ 606/103

(58) Field of Classification Search
CPC ........... A61B 17/1714; A61B 19/5244; A61B 17/1764; A61B 5/4533; A61F 2/0805; A61F 2/08; A61F 2/0811
USPC ......... 606/108, 88, 96–98, 103, 53, 232, 329, 606/80, 79, 87, 86 R; 623/20.35, 20.14, 623/20.32, 13.11, 13.14, 13.12
See application file for complete search history.

(56) References Cited

U.S. PATENT DOCUMENTS

| 4,509,516 | A | | 4/1985 | Richmond | |
|---|---|---|---|---|---|
| 4,883,048 | A | * | 11/1989 | Purnell et al. | 606/96 |
| 4,966,143 | A | * | 10/1990 | Meinershagen | 606/103 |
| 4,997,434 | A | | 3/1991 | Seedhom et al. | |
| 5,089,003 | A | | 2/1992 | Fallin et al. | |
| 5,163,940 | A | * | 11/1992 | Bourque | 606/96 |
| 5,269,786 | A | * | 12/1993 | Morgan | 606/96 |
| 5,350,383 | A | * | 9/1994 | Schmieding et al. | 606/96 |
| 5,496,326 | A | | 3/1996 | Johnson | |
| 5,713,897 | A | | 2/1998 | Goble et al. | |
| 5,810,864 | A | * | 9/1998 | Schaller | 606/170 |
| 5,879,353 | A | | 3/1999 | Terry | |
| 5,891,147 | A | | 4/1999 | Moskovitz et al. | |
| 6,171,310 | B1 | * | 1/2001 | Giordano et al. | 606/60 |
| 7,235,074 | B1 | | 6/2007 | Sklar | |
| 7,458,975 | B2 | | 12/2008 | May et al. | |
| 8,444,652 | B2 | * | 5/2013 | Amis et al. | 606/96 |
| 2010/0249497 | A1 | | 9/2010 | Peine et al. | |
| 2011/0071544 | A1 | | 3/2011 | Steger, Jr. et al. | |
| 2012/0004731 | A1 | | 1/2012 | Viker | |
| 2012/0265205 | A1 | | 10/2012 | Steiner et al. | |

OTHER PUBLICATIONS

International Search Report and Written Opinion issued by the ISA/U.S. Receiving Office, from corresponding patent application Serial No. PCT/US13/65882; dated Jan. 14, 2014; 10 pages.

* cited by examiner

Primary Examiner — Pedro Philogene
(74) Attorney, Agent, or Firm — Barbara A. Wrigley; Oppenheimer Wolff & Donnelly LLP

(57) ABSTRACT

A surgical instrument for use in performing anterior cruciate ligament reconstructions includes an elongate body section having a handle portion for a user to grasp the instrument, and a head section having a curvilinear groove formed therein adapted for receiving and frictionally engaging a guide wire. The head section can include an end portion having a contour anatomically conforming to the femur. The instrument can direct a guide wire to an anatomic position on the femur.

19 Claims, 12 Drawing Sheets

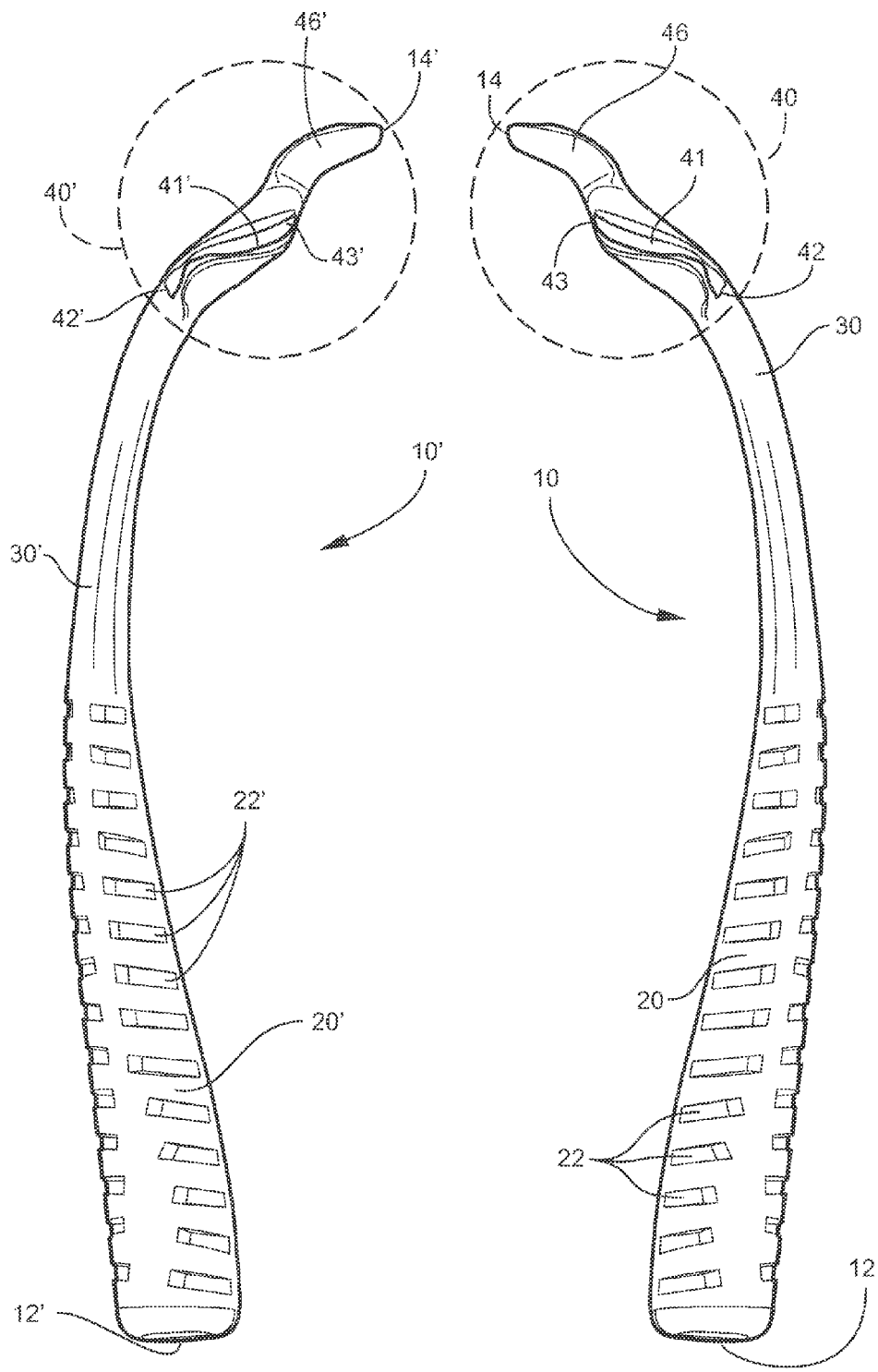

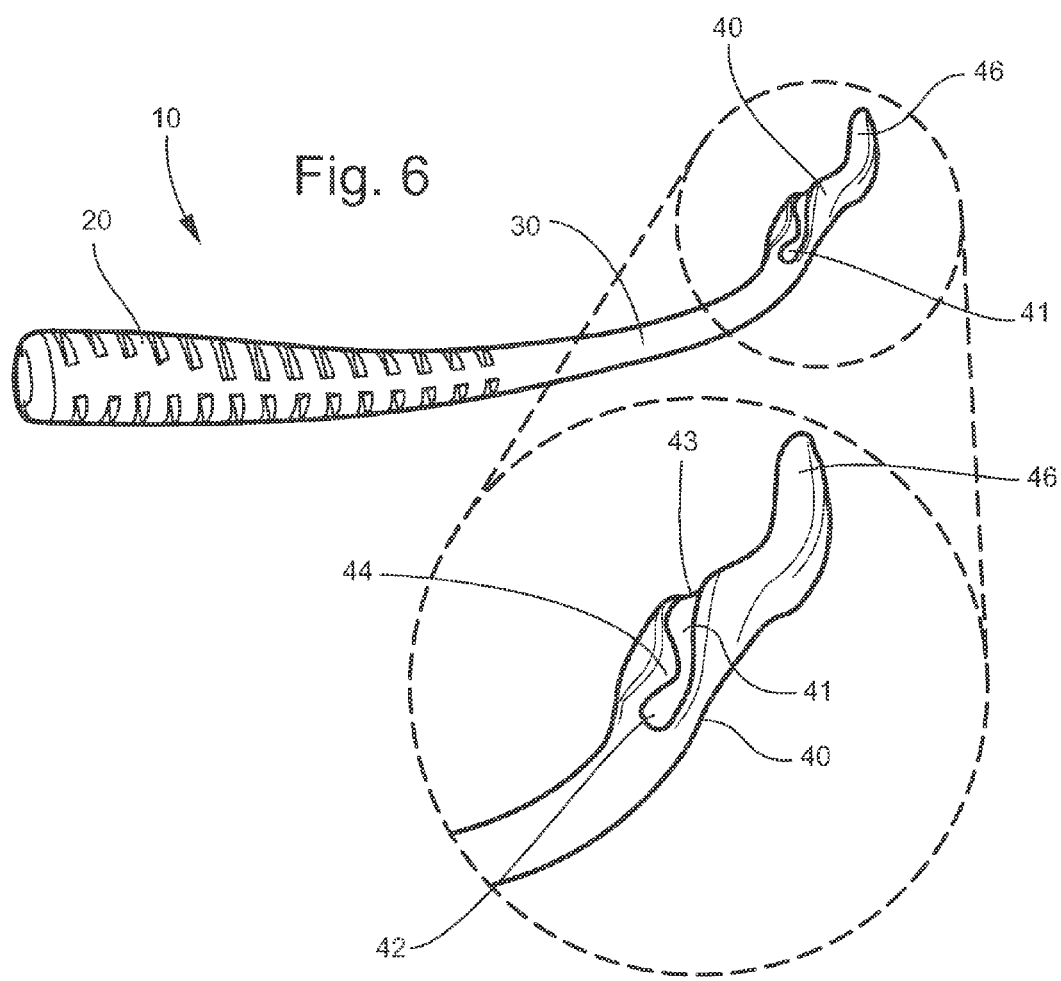

SURGICAL INSTRUMENT AND METHOD OF USING SAME

TECHNICAL FIELD AND BACKGROUND OF THE INVENTION

The present invention relates to a surgical instrument for use in performing anterior cruciate ligament reconstruction operations. The anterior cruciate ligament (ACL) is an important ligament in the center of the knee joint. The ACL stabilizes the knee during change-of-direction activities, such as in sports like soccer and basketball, preventing abnormal movement of the joint surfaces.

A torn ACL typically cannot be repaired, i.e., it will not heal, and therefore it must be reconstructed. ACL reconstruction involves replacing of the ligament with a similarly sized piece of tissue, known as a graft. Once healed in position, the graft is intended to function like a normal ACL.

A commonly performed technique for reconstructing the ACL is the "transtibial" technique. In this technique, a bone tunnel is drilled through the tibia such that the tunnel enters the knee joint where the ACL would normally attach. A drill guide is then inserted through the drilled tunnel to position a guide wire on the femur. A cannulated reamer is used to drill a second bone tunnel on the femur. A graft is then passed through the tibial tunnel, across the joint space and into the femoral tunnel. When the graft is fixed in position, it connects the two normal attachment points of the original ACL, thereby replicating the function of a normal ACL.

Recent medical studies suggest potential problems associated with the transtibial technique. A primary problem is that the tibial tunnel prevents the surgeon from positioning the guide pin for the femoral tunnel in an anatomic position. This is related to the orientation and rigidity of the tibial tunnel. Instruments passed through the tibial tunnel generally are not able to position the femoral tunnel correctly An alternative to the transtibial technique, is the AM portal technique. In this technique, a drill guide is passed through a small incision at the joint line, known as the anteromedial (AM) portal, rather than through the tibial tunnel. This technique allows better graft placement, but is technically much more difficult. It requires that the knee be bent much more during surgery, which decreases the surgeon's visibility, and has been associated with a higher complication rate. There are other ACL reconstruction techniques, but they are generally more cumbersome for the surgeon than the AM Portal technique.

Many practicing orthopedists were trained to perform ACL reconstructions using the transtibial technique, however, most orthopedists perform a relatively small number of ACL reconstruction surgeries each year. As such, the use of an unfamiliar and more complicated technique is less desirable among many practitioners.

SUMMARY OF THE INVENTION

Therefore, one object of the present invention is to provide a surgical instrument that allows for surgeons to perform ACL reconstructions utilizing some of the principles of the relatively easier transtibial technique, while providing the improved graft positioning associated with the more technically difficult AM portal technique. Another object of the present invention is to provide a surgical instrument that can improve both the ease and outcomes of ACL reconstructions. Yet another object of the invention is to provide a method of ACL reconstruction that resembles the transtibial technique with respect to technical ease, while providing an outcome with improved graft positioning resembling the more difficult AM portal technique.

These and other objects of the present invention can be achieved in the preferred embodiments of the invention described below. One embodiment of the invention comprises a surgical instrument comprising an elongate member having a first end and a second end opposite the first end. The instrument comprises a grippable handle section proximate the first end of the member, and a head section proximate the second end of the member. The head section has a groove formed therein having first and second ends, and a protuberance extends into the groove intermediate the first and second ends of the groove, such that the groove has a varying width, in which the width proximate the protuberance is narrowed relative to the width of the groove proximate the first end.

According to another embodiment of the invention, the handle section can be substantially cylindrical, and has a diameter that gradually decreases as the handle section extends from the first end of the member toward the second of the member.

According to another embodiment of the invention, the handle section can be ergonomically contoured, and has a knurled surface for facilitating a user's grip of the instrument.

According to another embodiment of the invention, the instrument includes an angled intermediate section between the handle section and the head section.

According to another embodiment of the invention, the intermediate section can be bent at an angle of fifty to eighty degrees.

According to another embodiment of the invention, the handle section and the intermediate section define a substantially cylindrical body having a diameter that is greatest where the handle section begins proximate the first end of the member, and gradually decreases until the intermediate section terminates at the head section.

According to another embodiment of the invention, the head section includes an arcuate end portion defining the second end of the member.

According to another embodiment of the invention, the width of the groove proximate the protuberance is less than the width of the groove proximate the first end and the second end.

According to another embodiment of the invention, a surgical instrument for use in performing anterior cruciate ligament reconstruction operations comprises an elongate body section having a handle portion for a user to grasp the instrument. The handle portion is positioned proximate the proximal end of the instrument, and a head section is proximate the distal end of the instrument. The head section has a curvilinear groove formed therein adapted for receiving and frictionally engaging a guide wire.

According to another embodiment of the invention, the curvilinear groove includes first and second ends, and a protuberance extends into the groove intermediate the first and second ends of the groove for frictionally engaging the guide wire within the groove.

According to another embodiment of the invention, the groove has a varying width, and the width proximate the protuberance is narrowed relative to the width of the groove proximate the first end and the second end.

According to another embodiment of the invention, rotation of the instrument in a first direction increases frictional engagement of the wire within the groove, and rotation of the instrument in a second direction opposite the first direction releases the wire from frictional engagement within the groove.

According to another embodiment of the invention, the body section includes an intermediate portion positioned between the handle portion and the head section, and the intermediate portion is bent at an angle such that the instrument can be leveraged against a posterior cruciate ligament.

According to another embodiment of the invention, the body section can be substantially cylindrical, and has a diameter that gradually decreases as the body section extends from the first end of the instrument toward the head section.

According to another embodiment of the invention, the handle portion is contoured, and has a plurality of channels formed therein for facilitating the user's handling of the instrument.

According to another embodiment of the invention, the head section includes an end portion having a contour anatomically conforming to the femur.

According to another embodiment of the invention, the instrument can be made of a transparent material, so that the user can see the guide wire pass through the groove.

According to another embodiment of the invention, a method of performing an anterior cruciate ligament reconstruction on a human knee includes providing a surgical instrument comprising an elongate body section having a handle proximate a first end of the instrument, and a head section having a curvilinear groove formed therein and an arcuate end portion having a contour anatomically conforming to a femur. A guide wire is provided for guiding a graft through a tibia to a desired anatomic position on a femur, and inserting the guide wire through the tibia. The head section is inserted through a portal proximate a joint line between the tibia and the femur, and the guide wire is inserted into the head section groove. The instrument is rotated in a first direction to frictionally engage the guide wire within the head section groove, and the instrument can be moved to direct the guide wire to the desired anatomic position on the femur.

According to another embodiment of the invention, the instrument can be rotated in a second direction opposite to the first direction to release the guide wire from frictional engagement with the head section groove.

BRIEF DESCRIPTION OF THE DRAWINGS

FIG. 1A is an enlarged partial view of the instrument of FIG. 1;

FIG. 2A is an enlarged partial view of the instrument of FIG. 2;

FIG. 4 is another perspective view of the instrument of FIG. 1;

FIG. 5 is a perspective view of a surgical instrument, according to another preferred embodiment of the invention;

FIG. 6 is another perspective view of the instrument of FIG. 1;

FIG. 6A is an enlarged partial view of the instrument of FIG. 6;

DESCRIPTION OF THE PREFERRED EMBODIMENTS OF THE INVENTION AND BEST MODE

Figure 1:
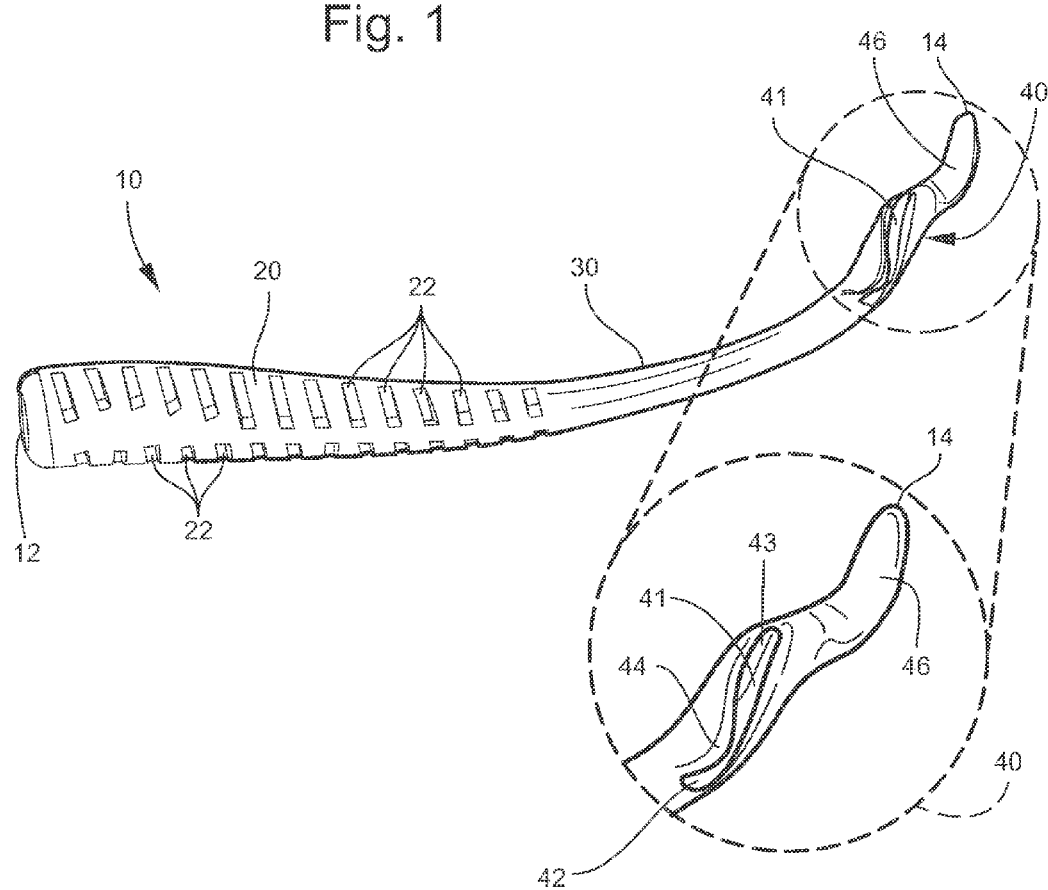
FIG. 1 is a perspective view of a surgical instrument according to a preferred embodiment of the invention.
Figure 2:
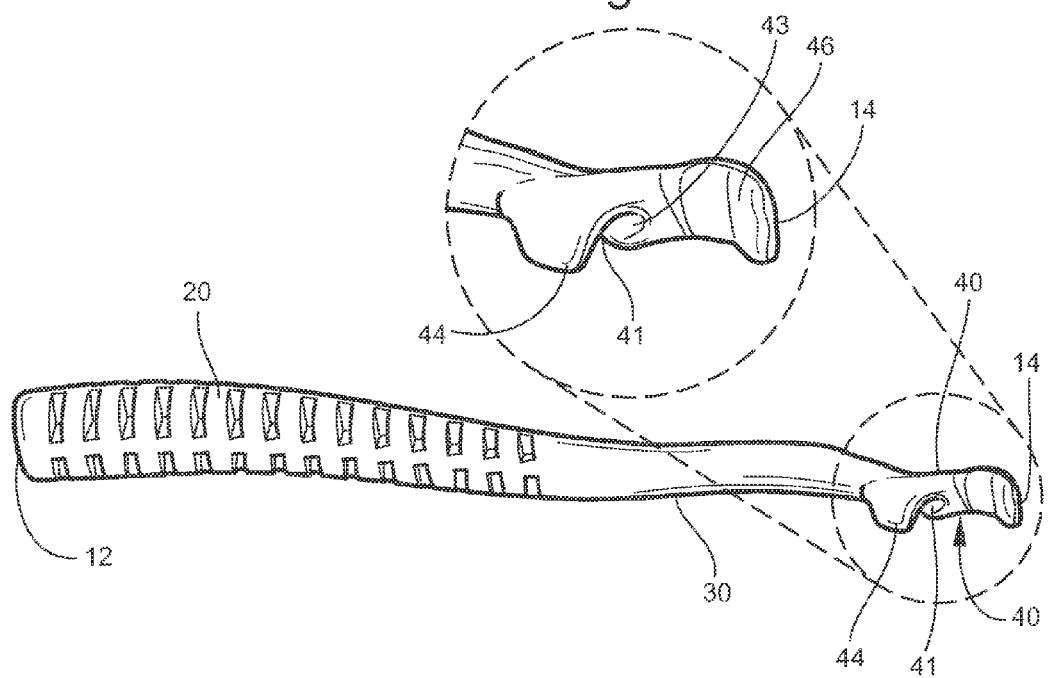
FIG. 2 is another perspective view of the instrument of FIG. 1.
Figure 3:
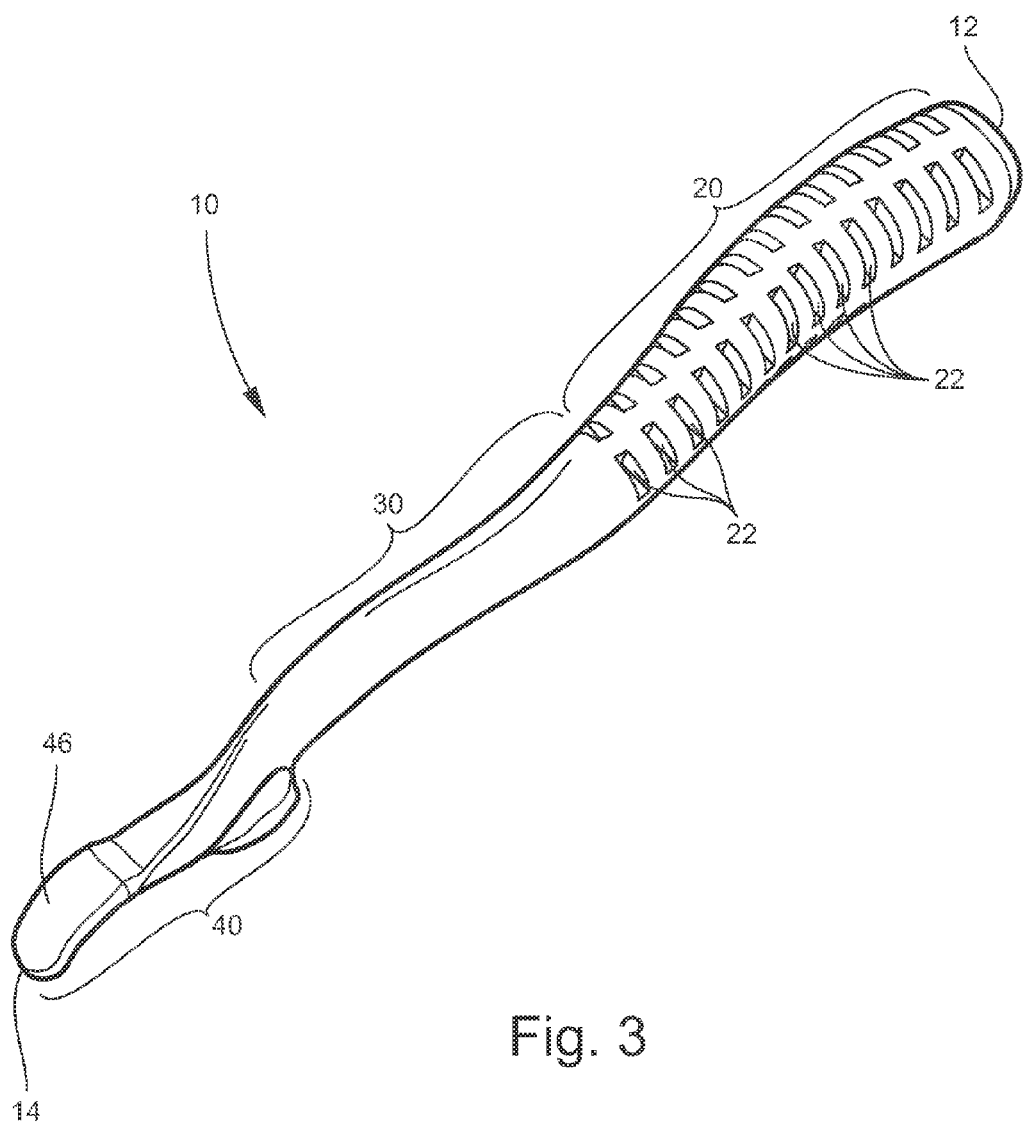
FIG. 3 is another perspective view of the instrument of FIG. 1.

A surgical instrument according to a preferred embodiment of the invention is illustrated in FIGS. 1-4, and shown generally at reference numeral 10. As shown in FIGS. 1-3, the surgical instrument 10 comprises an elongate member having a first proximal end 12, and a second distal end 14. The instrument 10 includes a grippable handle section 20 beginning at the proximal end 12, a head section 40 at the distal end 14, and an angled intermediate section 30 between the handle section 20 and the head section 40.

Figure 4A:
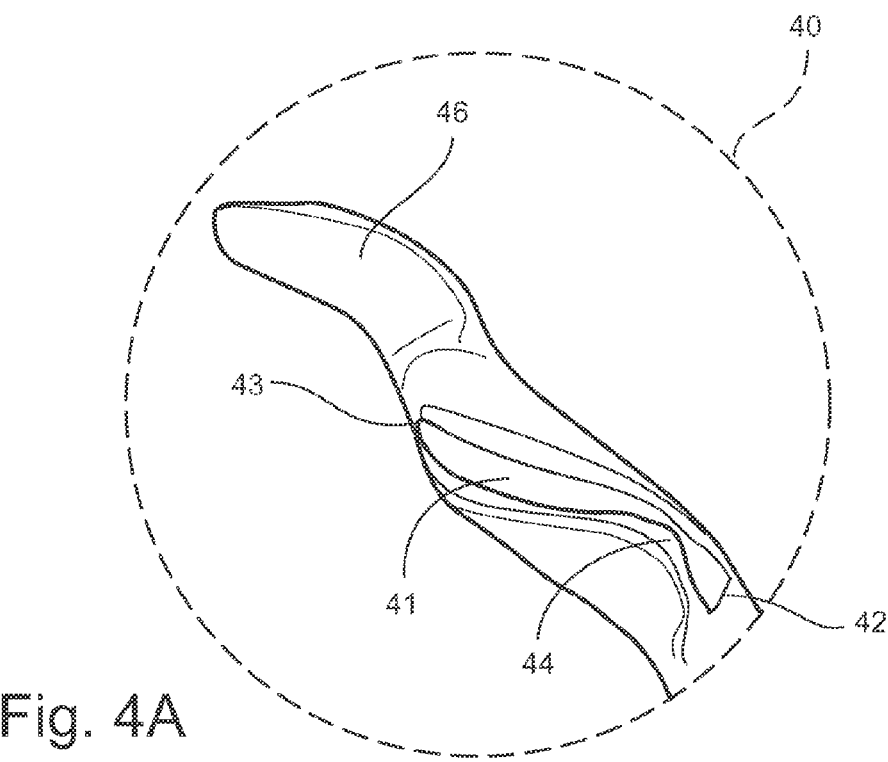
FIG. 4A is an enlarged partial view of the instrument of FIG. 4.

As shown in FIGS. 1A, 2A, 4A and 6A, the head section 40 has a curvilinear groove 41 formed therein having an entrance 42 and an exit 43. A protuberance 44 extends into the groove intermediate the first and second ends of the groove, whereby the groove has a varying width wherein the width proximate the protuberance is narrowed relative to the width of the groove at the entrance 42 and exit 43, as shown in FIGS. 1A, 4A, 6A. The head section 40 includes an arcuate end portion 46 located at the distal end 14 of the instrument 10, as shown in FIGS. 1A, 2A, 3 and 4A.

The handle 20 can be contoured, as shown in FIGS. 1-4, for ergonomic hold by the user. Also, the handle section 20 can have a knurled surface for facilitating ergonomic hold by the user. As shown in FIGS. 1, 3 and 4, the knurled surface can be comprised of a series of channels 22 formed in the handle section 20.

The intermediate section 30 can be bent at an angle, as shown in FIGS. 1 and 4. Preferably, the intermediate section 30 is bent at an angle of about fifty to eighty degrees.

The handle section 20 and intermediate section 30 define a generally cylindrical member having a diameter that is greatest where the handle section 20 begins at the proximal end 12 of the instrument 10, and gradually decreases until the intermediate section 30 terminates at the beginning of the head section 40, as shown in FIG. 3.

Figure 5A:
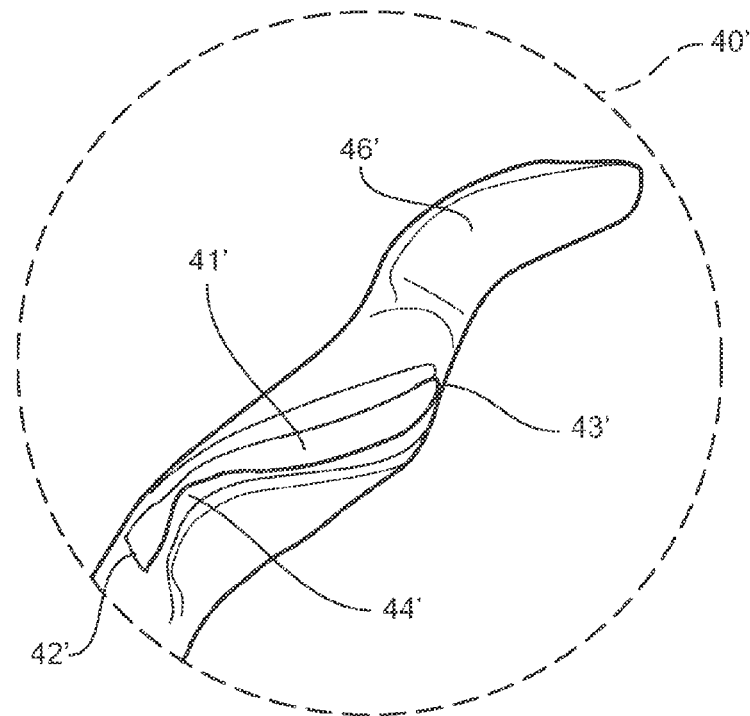
FIG. 5A is an enlarged partial view of the instrument of FIG. 5.

The instrument 10 can be used in performing surgery on the human knee, in particular, anterior cruciate ligament (ACL) reconstruction. As such, different versions for use on left and right knees. The instrument 10, illustrated in FIGS. 1-4, is a left knee version. An instrument for use in operating on right knees, according to a preferred embodiment of the invention, is illustrated in FIGS. 5, and shown generally at reference numeral 10'. The right knee version 10' can be a mirror image of the left knee version 10, as illustrated in FIGS. 4, 4A, 5, and 5A. The instrument 10' can be otherwise identical in structure to instrument 10.

A method of using the instrument 10, according to a preferred embodiment of the invention, is illustrated in FIGS. 7-11. As shown in Figures , the instrument 10 can be used to perform a transtibial technique anterior cruciate ligament (ACL) reconstruction procedure. It should be noted that Figures illustrate a method of using the instrument 10 in a left knee ACL reconstruction.

Figure 7:
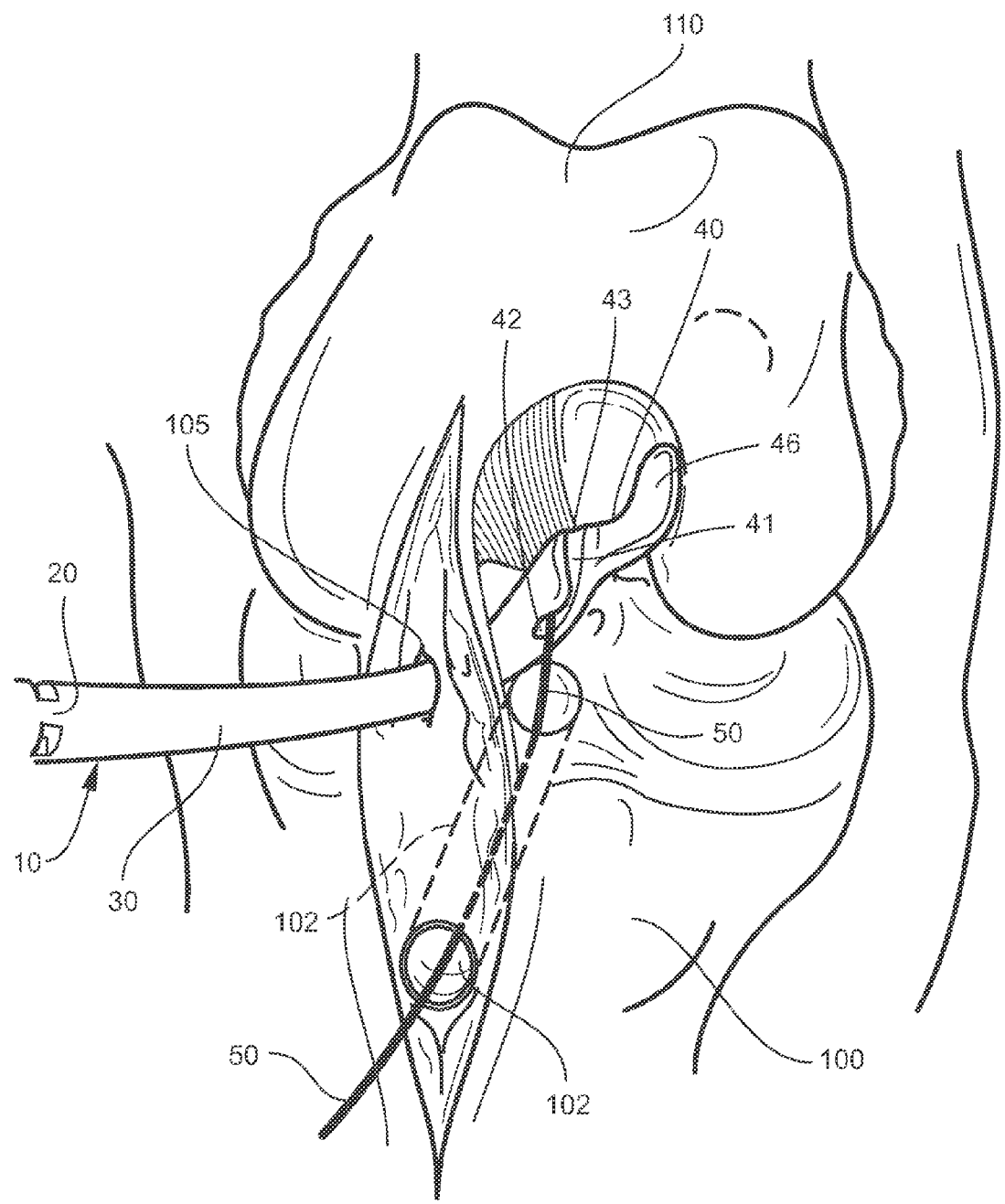
FIG. 7 is an environmental perspective view illustrating a method of using the instrument of FIG. 1, according to a preferred embodiment of the invention.
Figure 7A:
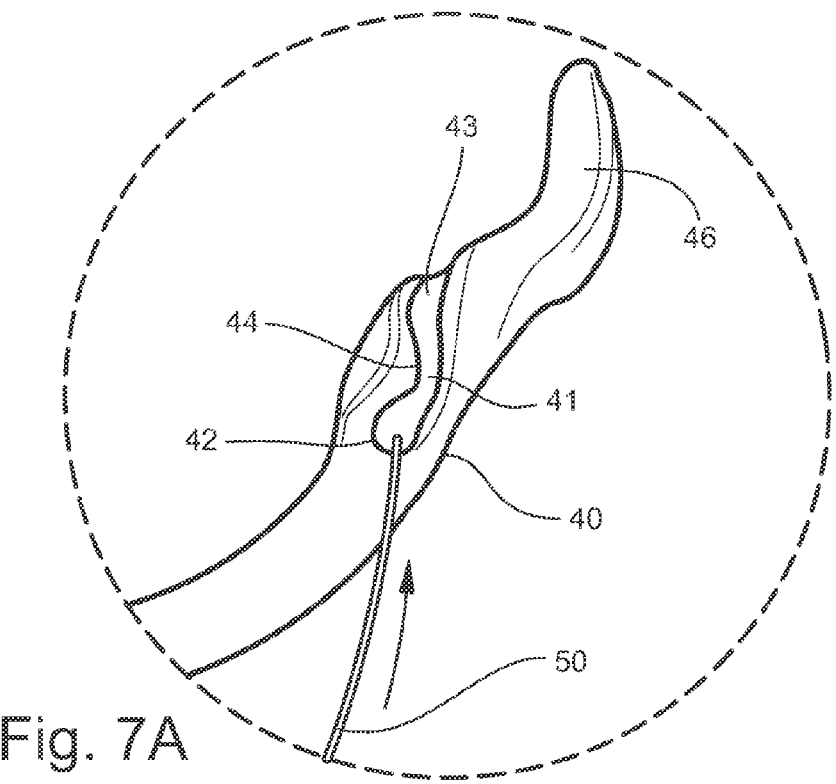
FIG. 7A is an enlarged partial schematic view of the instrument in FIG. 7.

A bone tunnel 102 is drilled through the tibia bone 100 such that the tunnel 102 enters the knee joint where the ACL would normally attach. A small incision is made at the joint line of the tibia 100 and femur 110, creating an anteromedial (AM) portal 105. As shown in FIG. 7, the distal end 14 of the instrument 10 is inserted through the AM portal 105. A guide wire 50 is passed through the transtibial tunnel 102, and inserted into the entrance 42 of the groove 41 of the head section 40, as shown in FIGS. 7 and 7A. The term "guide wire" as used herein refers generally to any elongate member, such as a wire or pin, that can be used in an ACL reconstruction to guide an ACL graft through the tibial tunnel 102 to an anatomic position on the femur 110.

Figure 9A:
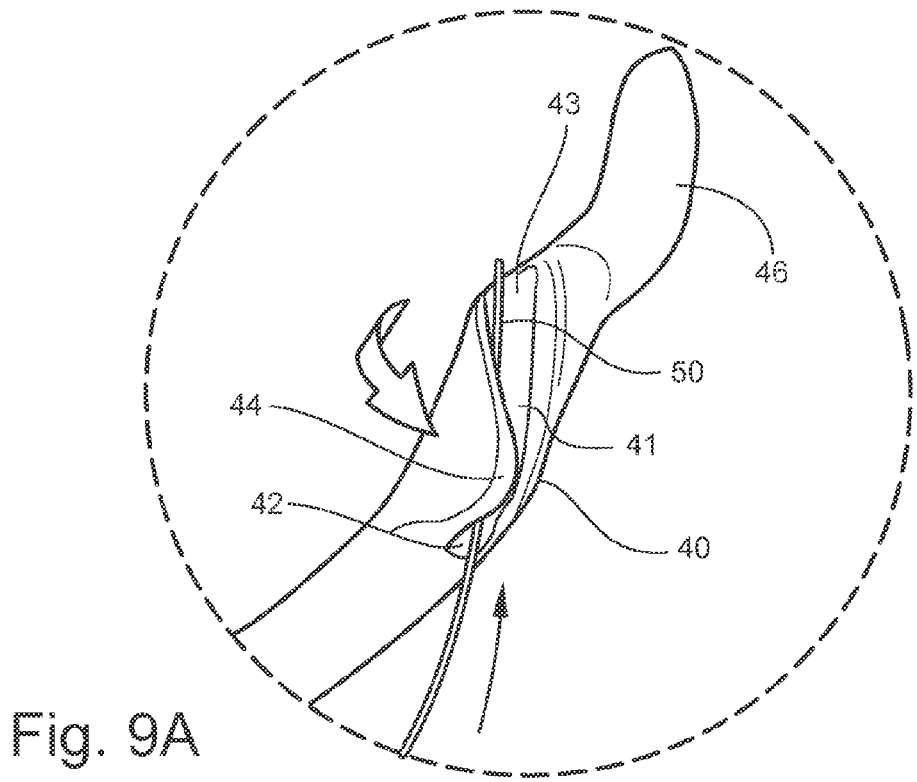
FIG. 9A is an enlarged partial schematic view of the instrument in FIG. 9.
Figure 8:
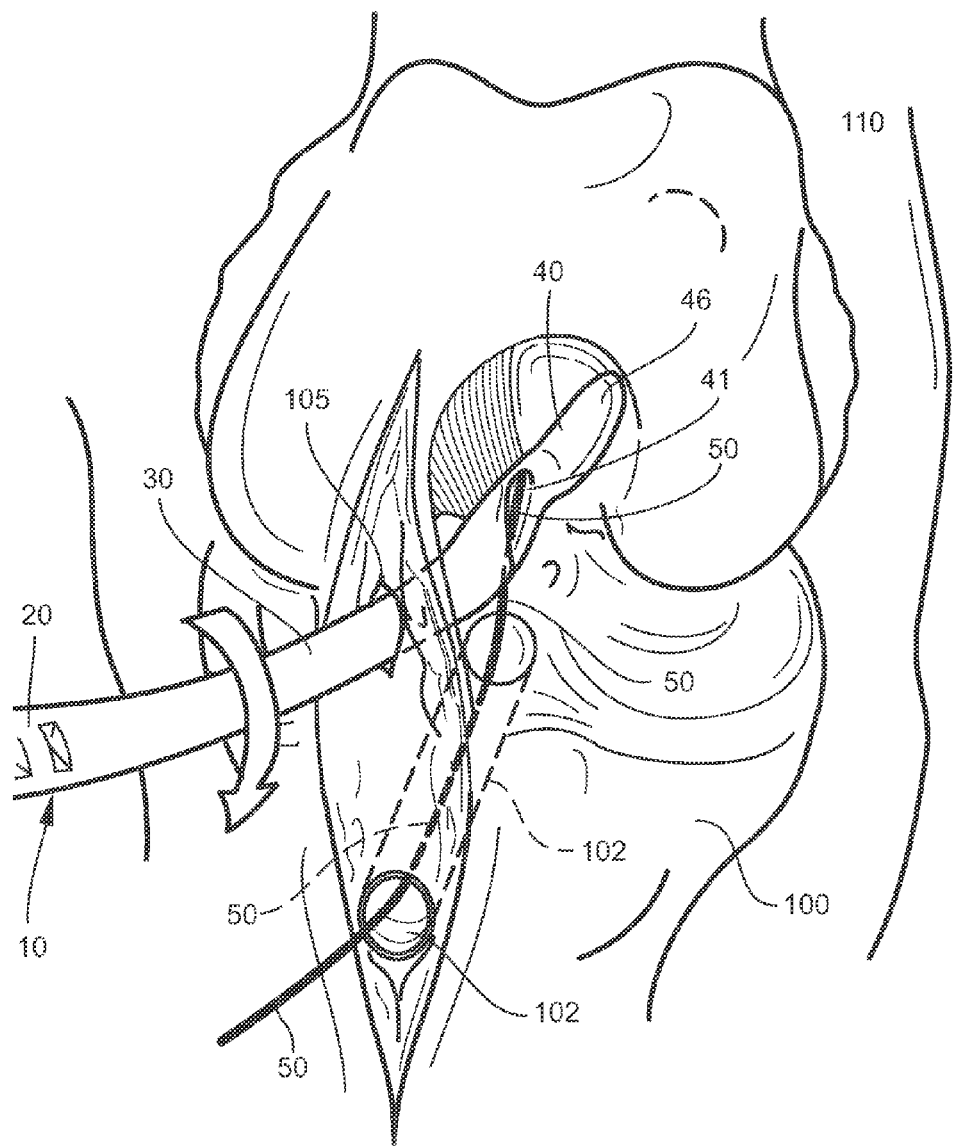
FIG. 8 is another environmental perspective view illustrating a method of using the instrument of FIG. 1, according to an embodiment of the invention.
Figure 9:
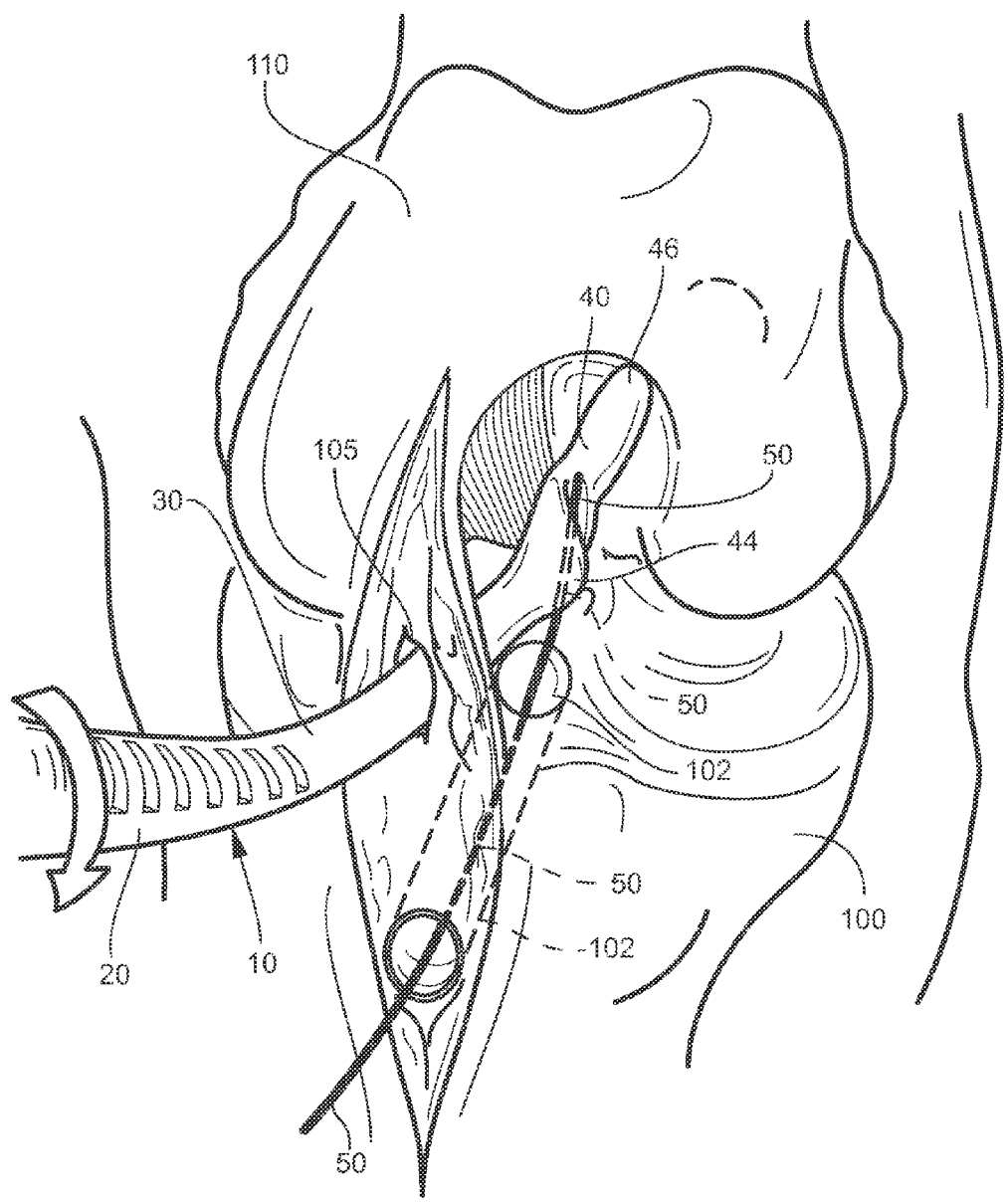
FIG. 9 is another environmental perspective view illustrating a method of using the instrument of FIG. 1, according to an embodiment of the invention.

The guide wire 50 is inserted into the groove 41, and the instrument 10 is rotated clockwise, as shown in FIG. 8, to capture the wire within the groove 41. As the instrument 10 is rotated clockwise, the protuberance 44 in the groove 41 engages the guide wire 50. Further clockwise rotation rotation of the instrument 10 increases the frictional engagement. As shown in FIGS. 9 and 9A, the instrument is rotated inwardly toward the wire 50 until the protuberance 44 engages the wire 50 such that it is securely held within the groove 40 of the head section.

Figure 10:
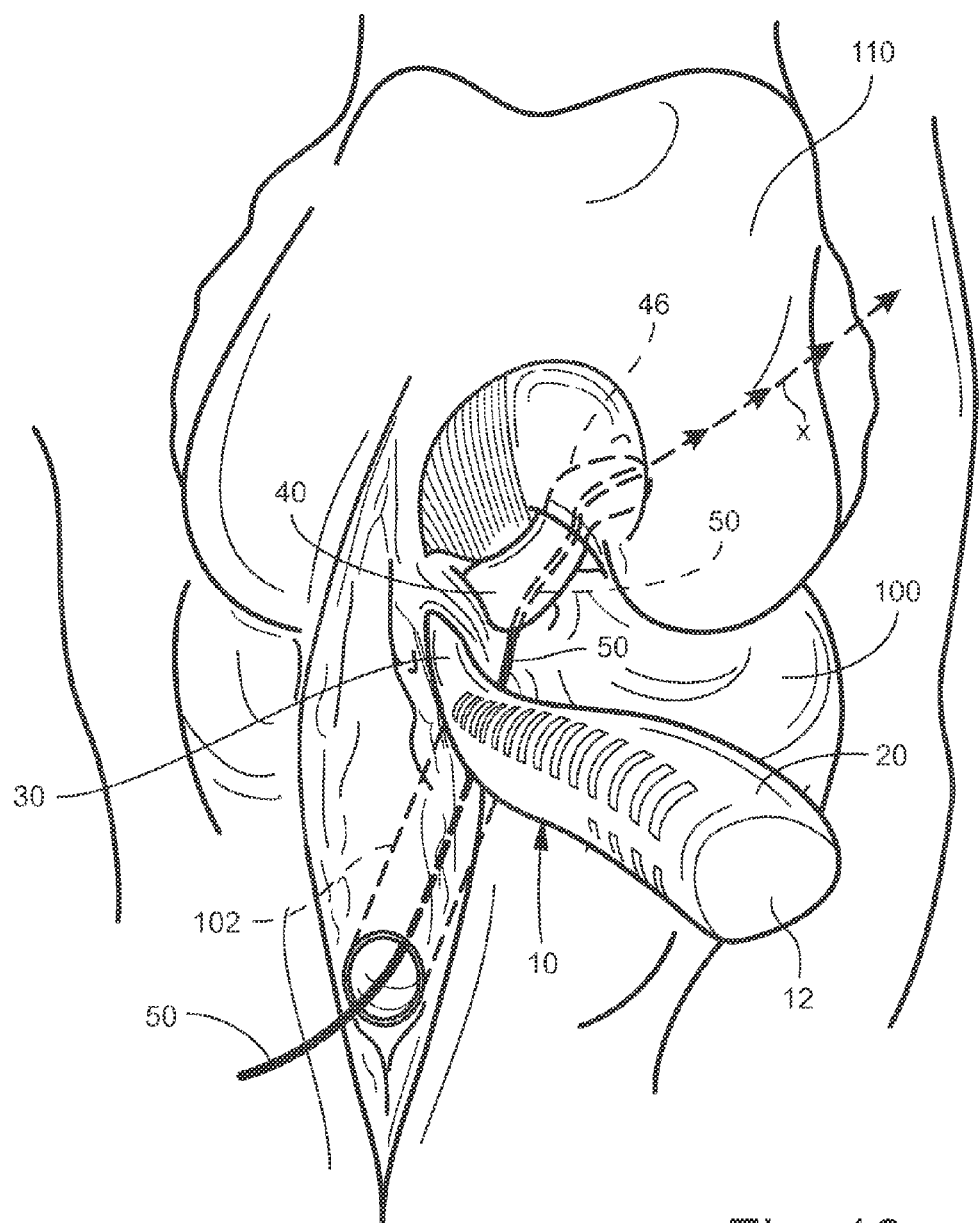
FIG. 10 is another environmental perspective view illustrating a method of using the instrument of FIG. 1, according to an embodiment of the invention.

With the wire 50 securely held within the groove 41, the instrument 10 is moved to be directly apposed to the femur 110, and the arcuate end portion 46 is hooked around the femur 110, as shown in FIG. 10. The anatomic contouring of the end portion 46, in combination with the curvilinear orientation of the interior of the groove 41, directs the wire 50 to a desired anatomic position on the femur 110. The end portion 46 of the head section 40 anatomically conforms to the normal bony contour of the femur 110. When apposed to the femur 110, the contour of the end portion 46 automatically positions the exit 43 of the head section groove 41 at the center of the ACL's normal attachment. Broken arrows designated with reference letter X, illustrates the trajectory of the guide wire 50. The wire 50 is guided by the instrument 10 to the proper anatomic position on the femur 110, as the wire is drilled into the femur 110 through the femoral tunnel 112.

Figure 11:
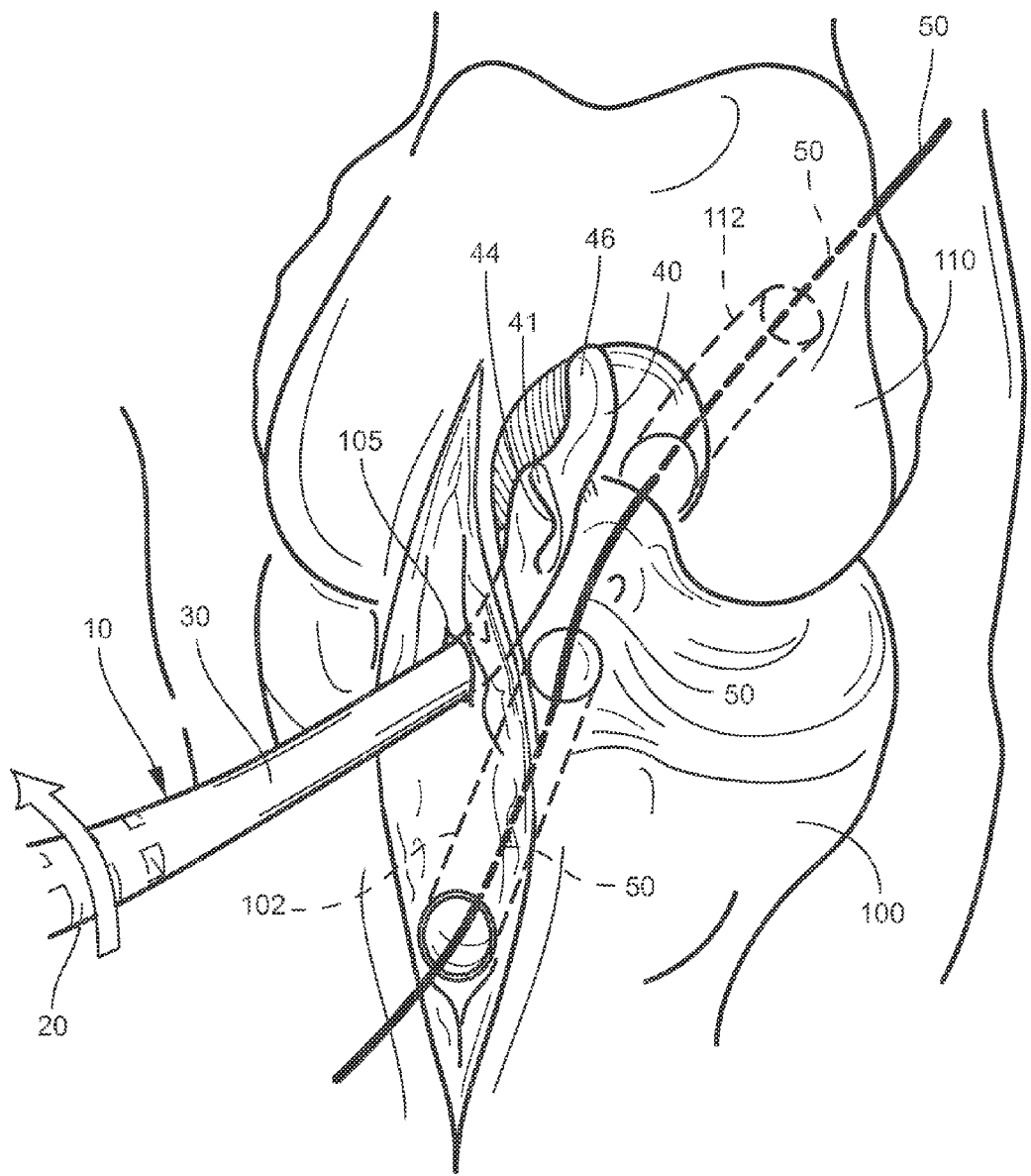
FIG. 11 is another environmental perspective view illustrating a method of using the instrument of FIG. 1, according to an embodiment of the invention.

When the wire 50 has been drilled into and positioned anatomically on the femur bone 110, the instrument 10 is rotated counterclockwise, thereby disengaging the wire 50 from the groove 41, as shown in FIG. 11. The curvilinear groove 41 in the head section 40 provides just enough constraint to allow appropriate direction of the guide wire 50, while also being flexible enough to allow the instrument 10 to be removed from the wire 50 after the wire 50 has been drilled into position on the femur.

The instrument 10 is removed, and the guide wire 50 can be used to pull the ACL graft through the tibial tunnel 102 and femoral tunnel 112 for attachment to the anatomic position on the femur 110. The remainder of the operation can proceed identically to a conventional transtibial technique ACL reconstruction. Hyper flexion of the knee is not required, as in conventional AM Portal technique ACL reconstruction, thereby improving visualization for the surgeon and speed of the operation. In addition, the ultimate result is a graft positioned in a more effective and anatomic fashion.

As noted above, FIGS. 7-11 illustrate the use of the instrument 10 in a left knee ACL reconstruction. The right knee version 10' can be used in a right knee ACL reconstruction, utilizing the same method described above, except that the instrument 10' is rotated counter-clockwise to engage the guide wire, and rotated clockwise to disengage the guide wire from the instrument 10'.

Because the groove 41 of the head 40 is open, the instrument 10 can be inserted from a location separate from the guide wire 50. This allows the instrument 10 to apply a directive force to the wire 50 without being influenced by the tibial tunnel 102. In contrast, prior art instruments for ACL reconstruction typically have a "closed" construction that requires that they be passed along the same path that the guide wire takes.

The curvilinear groove 41 and overhanging protuberance 44 of the head 40 provide an element of constraint to the wire 50 when the instrument 10 is rotated inwardly. Once the wire 50 is engaged in the groove 41, the instrument 10 can be used to direct the wire 50 where the surgeon wants it to go.

The end portion 46 of the head 40 conforms to the bony contour of the femur 110. The orientation of the interior of the groove 41 relative to the end portion 46 directs the guide wire 50 in a specific trajectory that avoids the back of the femur 110, and exits the femur 110 in a safe location. This specific trajectory results in a sufficiently long and intact bone tunnel.

The bend in the intermediate section 30 of the instrument 10 allows the instrument to be levered against the posterior cruciate ligament (PCL), the ligament directly adjacent to the ACL, both protecting the PCL and providing additional stability to the relationship of the groove 41 and end portion 46 of the head 40 with the femur 110. It also allows the surgeon to see the passage of the wire 50 from the tibial tunnel 102 into the groove 41 of the instrument 10. In the event that the surgeon decides to pass the wire 50 into the instrument 10 from a separate location, i.e. an accessory central portal, this allows for the surgeon's visualization of the passage of the wire 50.

The gripped and contoured handle 20 provide for ergonomic hold by the surgeon, optimizing leverage in providing additional stability to the instrument 10 as the wire 50 is passed therethrough.

The instrument can be made of stainless steel, a medical grade plastic such as polycarbonate-ISO or other suitable material. Preferably, the instrument 10 is made from a medical grade transparent plastic. As such, the instrument 10 is transparent, thereby allowing for visualization of the wire 50 as it passes through the groove 41 during drilling. The transparent instrument 10 can include opaque guide markings to assist the surgeon with placement of the device on the femur 110.

A surgical instrument and method of using same are described above. Various changes can be made to the invention without departing from its scope. The above description of the preferred embodiments and best mode of the invention are provided for the purpose of illustration only and not limitation—the invention being defined by the following claims and equivalents thereof.

What is claimed is:

1. A surgical instrument comprising an elongate member having a first end and a second end opposite the first end, the instrument comprising:
   (a) a grippable handle section proximate the first end of the member; and
   (b) a head section proximate the second end of the member, the head section having a groove formed therein having first and second ends, wherein a protuberance extends into the groove intermediate the first and second ends of the groove, whereby the groove has a varying width wherein the width proximate the protuberance is narrowed relative to the width of the groove proximate the first end.

2. A surgical instrument according to claim 1, wherein the handle section is substantially cylindrical, and has a diameter that gradually decreases as the handle section extends from the first end of the member toward the second of the member.

3. A surgical instrument according to claim 1, wherein the handle section is ergonomically contoured, and has a knurled surface for facilitating a user's grip of the instrument.

4. A surgical instrument according to claim 1, further comprising an angled intermediate section between the handle section and the head section.

5. A surgical instrument according to claim 4, wherein the intermediate section is bent at an angle of fifty to eighty degrees.

6. A surgical instrument according to claim 4, wherein the handle section and the intermediate section define a substantially cylindrical body having a diameter that is greatest where the handle section begins proximate the first end of the member, and gradually decreases until the intermediate section terminates at the head section.

7. A surgical instrument according to claim 1, wherein the head section further comprises an arcuate end portion defining the second end of the member.

8. A surgical instrument according to claim 1, wherein the width of the groove proximate the protuberance is less than the width of the groove proximate the first end and the second end.

9. A surgical instrument for use in performing anterior cruciate ligament reconstruction operations comprising:
   (a) an elongate body section comprising a handle portion for a user to grasp the instrument, the handle portion positioned proximate a first end of the instrument; and
   (b) a head section proximate a second end of the instrument opposite the first end, the head section having a curvilinear groove formed therein adapted for receiving and frictionally engaging a guide wire, wherein said curvilinear groove includes first and second ends, and a protuberance extending into the groove intermediate the first and second ends of the groove for frictionally engaging the guide wire within the groove.

10. An instrument according to claim 9, wherein the groove has a varying width, and the width proximate the protuberance is narrowed relative to the width of the groove proximate the first end and the second end.

11. An instrument according to claim 9, wherein frictional engagement of the guide wire within the groove increases as the instrument is rotated in a first direction toward the wire.

12. An instrument according to claim 11, wherein rotation of the instrument in a second direction opposite the first direction releases the wire from frictional engagement within the groove.

13. An instrument according to claim 9, wherein the body section includes an intermediate portion positioned between the handle portion and the head section, wherein the intermediate portion is bent at an angle whereby the instrument can be leveraged against a posterior cruciate ligament.

14. An instrument according to claim 9, wherein the body section is substantially cylindrical, and has a diameter that gradually decreases as the body section extends from the first end of the instrument toward the head section.

15. A surgical instrument according to claim 9, wherein the handle portion is contoured and has a plurality of channels formed therein for facilitating the user's handling of the instrument.

16. A surgical instrument according to claim 9, wherein the head section further comprises an end portion having a contour anatomically conforming to the femur.

17. A surgical instrument according to claim 9, wherein the instrument is comprised of a transparent material, whereby the user can see the guide wire pass through the groove.

18. A method of performing an anterior cruciate ligament reconstruction on a human knee comprising:
   providing a surgical instrument comprising an elongate body section having a handle proximate a first end of the instrument, and a head section having a curvilinear groove formed therein and an arcuate end portion having a contour anatomically conforming to a femur, the head section positioned proximate a second end of the instrument opposite the first end;
   providing a guide wire for guiding a graft through a tibia to a desired anatomic position on a femur, and inserting the guide wire through the tibia;
   inserting the head section through a portal proximate a joint line between the tibia and the femur;
   inserting the guide wire into the head section groove;
   rotating the instrument in a first direction to frictionally engage the guide wire within the head section groove; and
   moving the instrument to direct the guide wire to the desired anatomic position on the femur.

19. A method according to claim 18, further comprising the step of rotating the instrument in a second direction opposite to the first direction to release the guide wire from frictional engagement with the head section groove.

* * * * *